United States Patent
Louie et al.

(10) Patent No.: US 7,672,859 B1
(45) Date of Patent: Mar. 2, 2010

(54) PRESCRIPTION ORDER POSITION TRACKING SYSTEM AND METHOD

(75) Inventors: Shelton Louie, Vancouver, WA (US); Stephen A. Garrett, Vancouver, WA (US); Mark B. Smith, Vancouver, WA (US)

(73) Assignee: GSL Solutions, Inc., Vancouver, WA (US)

( * ) Notice: Subject to any disclaimer, the term of this patent is extended or adjusted under 35 U.S.C. 154(b) by 0 days.

(21) Appl. No.: 09/715,439

(22) Filed: Nov. 16, 2000

(51) Int. Cl.
*A61B 5/00* (2006.01)

(52) U.S. Cl. .................. 705/3; 705/2; 705/22; 705/28; 235/462.46

(58) Field of Classification Search ............. 705/22–23, 705/28, 29, 26, 2–3, 7, 30; 340/10.1; 235/462.46
See application file for complete search history.

(56) References Cited

U.S. PATENT DOCUMENTS

| | | | | |
|---|---|---|---|---|
| 4,766,542 A * | 8/1988 | Pilarczyk | .................... | 705/3 |
| 5,593,267 A * | 1/1997 | McDonald et al. | .......... | 414/273 |
| 5,597,995 A * | 1/1997 | Williams et al. | ............ | 235/375 |
| 5,771,657 A * | 6/1998 | Lasher et al. | ................. | 53/55 |
| 5,794,213 A * | 8/1998 | Markman | .................. | 705/23 |
| 5,845,264 A * | 12/1998 | Nellhaus | ...................... | 705/28 |
| 5,907,493 A * | 5/1999 | Boyer et al. | ........... | 364/479.01 |
| 5,926,093 A * | 7/1999 | Bowers et al. | ............ | 340/572.1 |
| 5,936,527 A * | 8/1999 | Isaacman et al. | ......... | 340/572.1 |
| 5,996,889 A * | 12/1999 | Fuchs et al. | ................... | 705/22 |
| 6,021,392 A * | 2/2000 | Lester et al. | .................. | 705/2 |
| 6,057,756 A * | 5/2000 | Engellenner | ................ | 340/505 |
| 6,170,746 B1 * | 1/2001 | Brook et al. | ................ | 235/385 |
| 6,202,923 B1 * | 3/2001 | Boyer et al. | ................ | 235/375 |
| 6,219,587 B1 * | 4/2001 | Ahlin et al. | .................. | 700/233 |
| 6,223,137 B1 * | 4/2001 | McCay et al. | ................ | 702/184 |
| 6,249,212 B1 * | 6/2001 | Beigel et al. | ............. | 340/10.34 |
| 6,339,732 B1 * | 1/2002 | Phoon et al. | ................ | 700/237 |
| 6,354,493 B1 * | 3/2002 | Mon | ......................... | 235/380 |
| 6,448,886 B2 * | 9/2002 | Garber et al. | .............. | 340/10.1 |
| 6,450,406 B2 * | 9/2002 | Brown | .................... | 235/462.45 |
| 6,464,142 B1 * | 10/2002 | Denenberg et al. | ..... | 235/462.46 |
| 6,496,806 B1 * | 12/2002 | Horwitz et al. | ............... | 705/28 |
| 6,522,945 B2 * | 2/2003 | Sleep et al. | .................. | 700/225 |
| 6,564,121 B1 * | 5/2003 | Wallace et al. | .............. | 700/231 |
| 6,611,806 B1 * | 8/2003 | Harvey | ........................ | 705/2 |

* cited by examiner

*Primary Examiner*—Vanel Frenel
(74) *Attorney, Agent, or Firm*—Harness, Dickey & Pierce, P.L.C.

(57) ABSTRACT

An economical prescription order tracking system automatically monitors and tracks prescription orders through a conventional pharmacy. The system includes a tracking tag having a unique identifier associated with it secured near the prescription order such that it travels with the order through various locations within the pharmacy. Tag reading devices are positioned at key locations throughout the pharmacy to detect the location of each tag, and its associated attached prescription order. The detected locations are compiled via a computer system and associated with the customer, such that at any given time the location of the prescription order within the pharmacy can be determined, thereby facilitating the efficient operation of the pharmacy. Preferably, filled prescription orders are placed in a large bin having multiple cubbies within it. Each cubby has a displayed number and a tag reading device received therein such that the location of the prescription order within the cubby is easily determined simply by placing the prescription order with tag into an available cubby. The time each prescription order remains at each location and worker identity information at each location can be recorded and compiled to facilitate workflow and worker efficiency monitoring of the pharmacy.

16 Claims, 6 Drawing Sheets

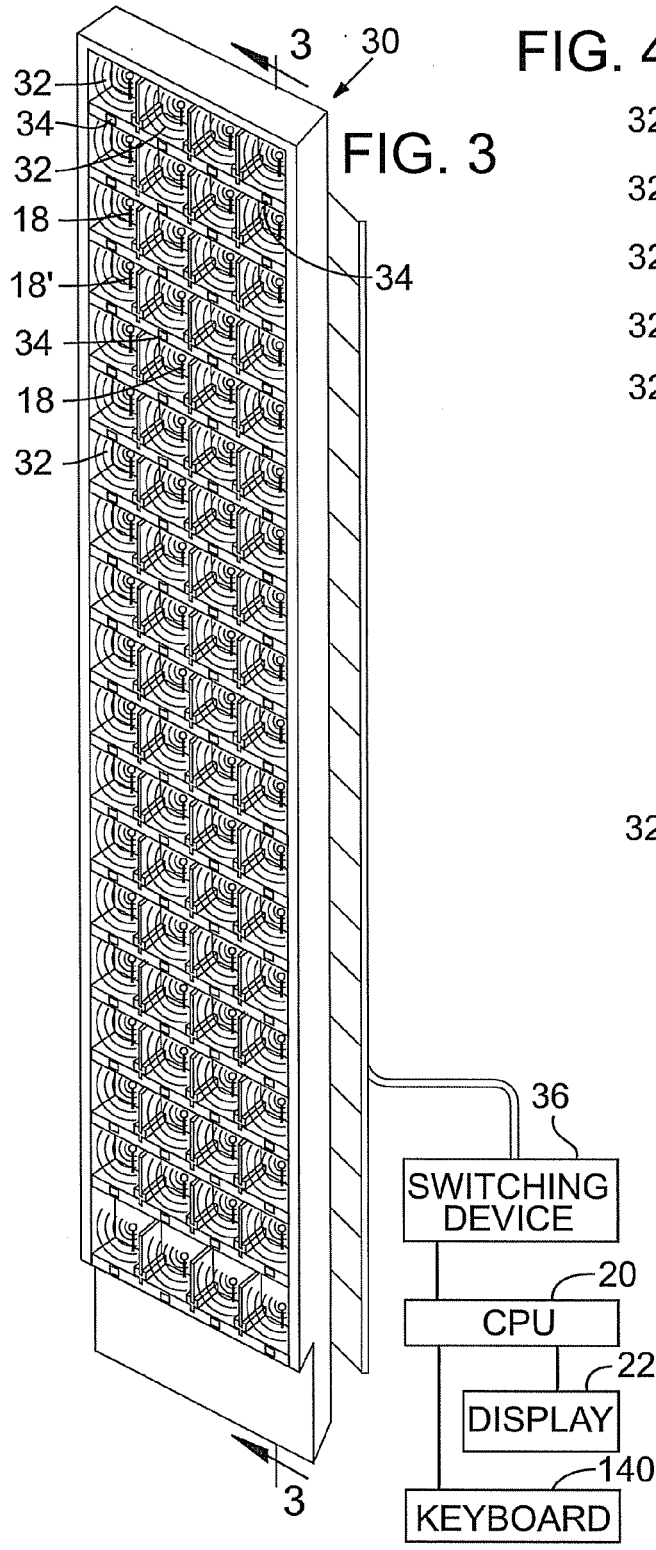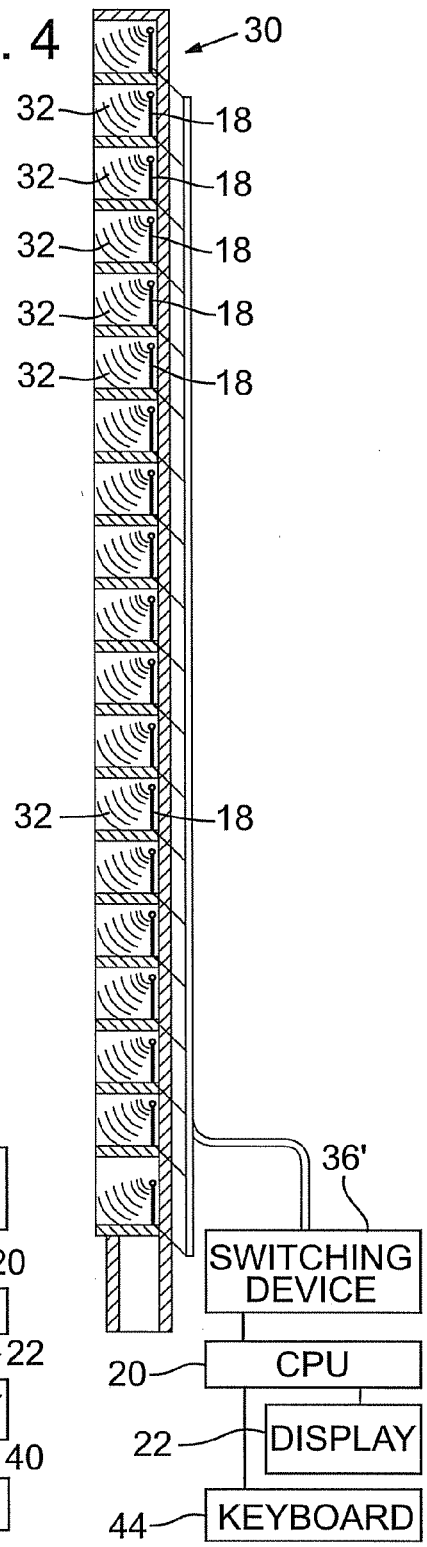

PRESCRIPTION ORDER POSITION TRACKING SYSTEM AND METHOD

FIELD OF THE INVENTION

The present invention relates to a system for tracking physical prescription orders being filled through a pharmacy. In particular, it includes an automated position sensing device for detecting and identifying the location of a physical prescription order as it travels within a pharmacy and ultimately is stored in a location for either customer pickup or filing.

BACKGROUND AND SUMMARY OF THE INVENTION

A typical local retail pharmacy fills thousands of prescription orders per week. Moreover, as the general population ages and new beneficial drugs are introduced, prescription order volumes to be filled at retail pharmacies are expected to double within the next few years. This present and expected increase in order volume places enormous pressure on pharmacists and other pharmacy workers, who strive to fill each order efficiently, accurately and quickly.

Most customers have a limited view of how a typical retail pharmacy works. They often think that when they present a written prescription order to a local retail pharmacy, such as at their corner drugstore, a pharmacist will personally greet them, review their order, complete and file the necessary paperwork required by applicable laws, fill the prescription order, and present the filled order to the customer, all within a few minutes. However, in addition to increasing volume, the traditional retail pharmacist is now faced with a large variety of additional tasks, including obtaining proper insurance payment authorization, and in some cases verifying the refillabilty of a particular prescription order. Moreover, orders may now enter the pharmacy through a wide variety of mediums, such as via facsimile, phone call, and e-mail.

In light of the increasing demands and obligations placed on retail pharmacies, they are evolving into more efficient organizations having numerous employees performing individual tasks associated with filling each prescription order. For example, when a customer presents a prescription to the pharmacy, a clerk may take the prescription order and enter it into a computer system that verifies insurance information. If approved, he or she may then prepare a prescription label to be placed on the package that will ultimately contain the prescribed drug. The clerk may then present the prescription order and label to a technician, usually stationed at another location within the pharmacy, who will physically fill the prescription by placing the appropriate quantity of the prescribed drug within the bottle and attach the label. Pursuant to applicable laws, a registered pharmacist then reviews the technician's work, and approves the dispersal of the completed prescription order to the customer. A clerk may then place the filled prescription in a storage area to await customer pick-up. Upon customer pick-up, the clerk files the written prescription order and any other appropriate paperwork related to the transaction, such as signed insurance forms and any informed consent paperwork. This type of system allows the pharmacy to quickly, efficiently, and economically fill numerous prescription orders.

Given the high volume of prescription orders being filled, the large number of people performing individual tasks associated with filling each prescription order, and the numerous locations within the pharmacy that a prescription order can be positioned as it is being filled, it is important that the prescription order, and ultimately the filled prescription, be easily located throughout the process. For example, if a particular prescription order is denied payment by insurance, a clerk may hold the prescription order aside while the customer is contacted. If the customer presents himself to another clerk at the pick-up window, while the first clerk is attempting to call the customer at home, the second clerk often has no way of knowing the current status of the prescription order, or where it is in the order filling process. Accordingly, the second clerk is forced to search each location within the pharmacy. Similarly, should a prescription order be inadvertently misplaced within the pharmacy, it is often difficult to find, thereby needlessly delaying the filling process and wasting worker time to locate it.

Some pharmacy vendors have attempted to overcome these problems by offering systems that manually track prescription orders within a pharmacy. In particular, they require the worker at a given station to manually enter into a computer the fact that they have received a particular prescription order at that particular location. Some of these systems also require the pharmacy support worker to manually enter into the computer the fact that the prescription order has left their station, or to identify the new station where they delivered the prescription order.

However, such manual tracking systems require considerable pharmacy support worker time and attentiveness to be used effectively. For example, if it takes a worker 20-60 seconds to manually enter the location of each prescription order that arrives at a particular worker's station, and that station typically handles 3000-6000 prescription orders per week, then 25-50 hours per week per station would be spent entering this information. If there are numerous stations within the pharmacy, the total time spent within the pharmacy manually entering such information could easily exceed several hundred hours per week. Moreover, should a worker fail to enter the location of a particular prescription order, any attempt to locate that prescription order using the available location information will lead a worker to only the last known location of the prescription order. Accordingly, an inefficient manual tracking of the prescription order would still be required, rendering the manual location device useless.

Similarly, some pharmacy vendors have attempted to automate the prescription filling aspect of a pharmacy by incorporating an automatic assembly line process for filling prescription orders. In particular, an operator enters a prescription order into a computer system, which causes a conveyor-type system to deliver an empty vial to an automated drug dispenser. The filled vial is then automatically matched with a label and presented to a pharmacist for final review and approval. While these types of devices facilitate the quick and efficient filling of prescription orders, they are expensive for use in a retail pharmacy environment, and they occupy a large amount of limited space within the pharmacy. Moreover, they still require pharmacy workers to perform manual tasks such as verifying insurance and renewability of the prescription, and processing the various forms of prescription orders before and after they are entered into the automated system. Accordingly, they do not permit the easy tracking of prescription orders as they travel within the automated pharmacy environment.

The present invention overcomes these and other problems with known prescription order tracking systems. It is an economical and automatic prescription order tracking system that monitors and tracks prescription orders through a retail pharmacy. Preferably, a tracking tag having a unique identifier associated with it, is attached to the prescription order, which could be a written prescription form 44 (FIG. 6B), a prescription label 42 (FIG. 6A), or any other tangible medium documenting a request for prescription by a health care provider. Tag reading devices are positioned at key locations throughout the retail pharmacy to detect the location of each tag, and its associated attached prescription order. The detected locations are compiled via a computer system and associated with the customer, such that at any given time the location of the prescription order within the retail pharmacy can be quickly and easily determined.

Filled prescription orders can be placed in a large bin having multiple cubby holes within it. Each cubby hole has a displayed number and a tag reading device received therein. When a pharmacy worker places a filled prescription and the prescription order having the tag attached into an available cubby, the tag reading device within that selected cubby detects the location of that prescription and paperwork and reports that location to the computer system. Accordingly, when a customer arrives to pick-up their prescription, a pharmacy worker need only enter the customer's identifying information into the computer system and the number of the specific cubby containing the filled prescription and prescription order can be located.

In one preferred embodiment, the tags are unique bar codes, and the tag reading devices are bar code scanners positioned throughout the retail pharmacy. In an alternative preferred embodiment, the tags are electromagnetic antenna and the like, and the tag readers are limited range transponders and the like as disclosed in U.S. Pat. No. 6,057,756 to Engellenner, that automatically detect the location of the attached prescription order as it enters and leaves predetermined locations within throughout the pharmacy. The tag readers can be fixed at the particular locations, or portable (i.e. handheld) to facilitate scanning of prescription orders that are compiled in bulk.

The tags themselves can be either rigidly or detachably secured to the prescription order. For example, the tags can be directly secured to the prescription with adhesive or secured within a prescription lid. Also, the tags can be secured to a fastener, such as a paperclip, that is detachably secured to the prescription order. Alternatively, the tag can be rigidly secured to a carrier, such as a basket, and the prescription order and materials related to filling the prescription can be placed in the same carrier throughout the prescription filling process.

Additional objects and advantages of the present invention will be apparent from the detailed description of the preferred embodiment thereof, which proceeds with reference to the accompanying drawings.

BRIEF DESCRIPTION OF THE DRAWINGS

FIG. 3 is an isometric view of a prescription storage bin in accordance with a preferred embodiment of the present invention.

FIG. 4 is the prescription storage bin of FIG. 3 taken along lines 4-4 of FIG. 3.

DETAILED DESCRIPTION OF PREFERRED EMBODIMENTS

An economical and automatic prescription order tracking system 10 that monitors and tracks prescription orders 12 through a pharmacy 14 is shown in FIGS. 1-8

Figure 1:
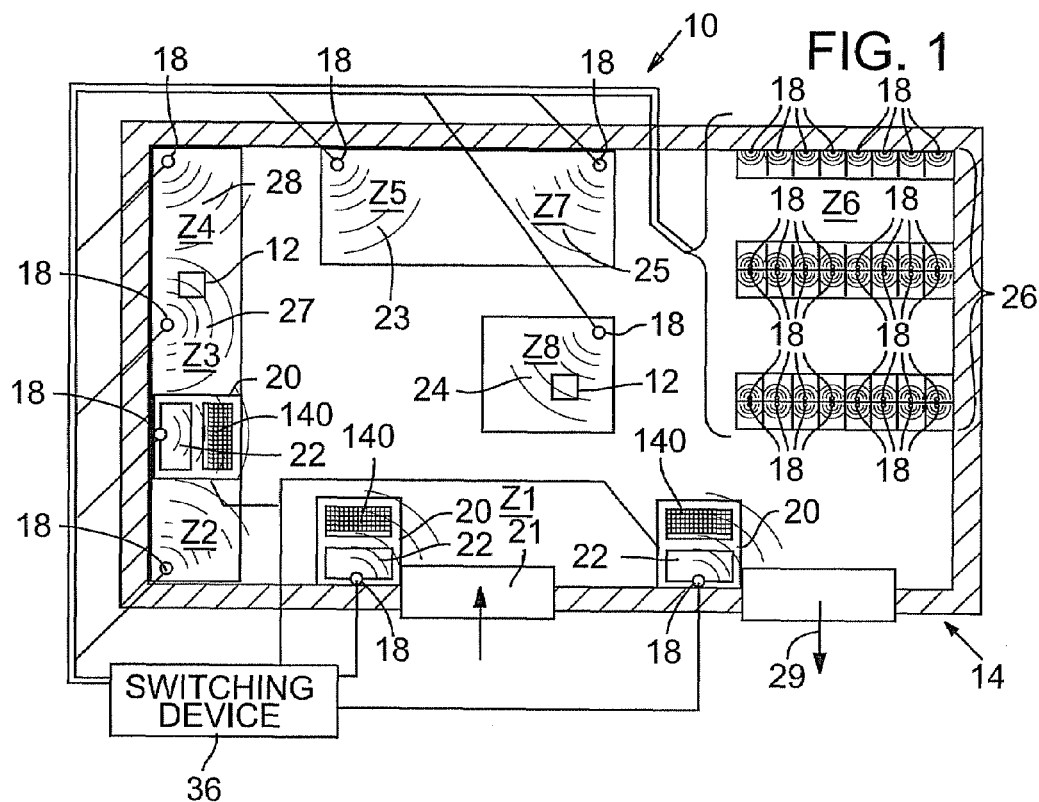
FIG. 1 is a schematic view of a prescription order tracking system in accordance with a preferred embodiment of the present invention.
Figure 5:
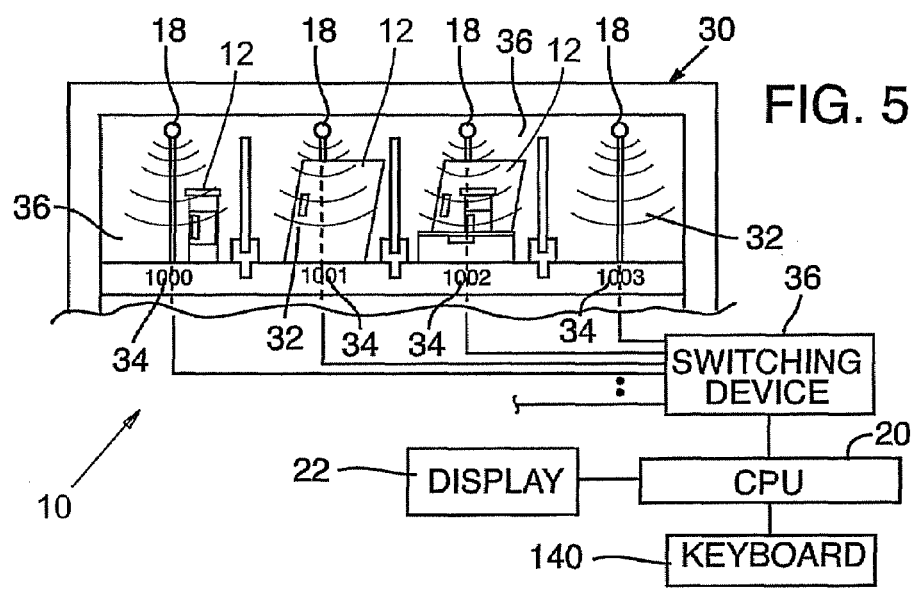
FIG. 5 is a fragmentary view of the prescription storage bin of FIG. 3 taken along lines 5-5 of FIG. 3.

In general and as best shown in FIGS. 1, 3, and 5, a prescription order 12 is presented to the pharmacy 14 and assigned an identification tag 16. Tag reading devices 18 are positioned at key locations throughout the pharmacy 14 and in communication with a computer system 20 having a display 22, such that the movement of the prescription order 12 throughout the pharmacy 14 automatically detects and records the location of the tag 16 without further worker input. Accordingly, a worker can easily determine the location of the prescription order 12 within the pharmacy by entering commands in the computer system 20 with a user input device such as a keyboard 120 to display the location of the prescription order 12 on the computer display 22. The individual elements forming the present invention are discussed in greater detail below.

A. Exemplar Tracking Devices

The tags 16 of the tracking devices should be light weight and economical. One such known device is a bar code label, which would be used in conjunction with multiple bar code scanners serving as the tag reading device. One such device is disclosed in U.S. Pat. No. 4,210,802 to Sakai, the disclosure of which is hereby incorporated by reference. A bar code scanner would be placed at each station and serves as the tag reading device 18. The worker in that area would simply scan the label as it entered into the area. Each scanner would then be placed in communication with the computer system 20 such that information regarding the customer, his prescription order position, and the status of his order can be readily displayed on the computer system display 22.

Alternatively, an even more automated tracking system that may be used includes using known devices that can locate objects through electromagnetic interrogation of a spatial region to determine the presence of an object. One such system is disclosed in U.S. Pat. No. 6,057,756 to Engellenner, the disclosure of which is hereby incorporated by reference. In general, the tag 16 is an electromagnetic antenna and/or signal receiver which responds either passively or actively to announce the presence (or absence) of an object within a controlled region defined by a broadcasted electromagnetic interrogation signal. Preferably, each tag 16 includes a coding mechanism for uniquely identifying it with respect to other tags in the system.

The tag reading device 18 is preferably one or more interrogation signal generators, or search beacons, that are simple electromagnet field generators (e.g., radio transmitters or magnetic field coils) which cause specific tags to respond.

More preferably, the tag reading devices 18 are transceivers that both transmit an interrogation signal and receive a response signal, echo, or otherwise send a field perturbation, indicating the presence of a specified tagged item within the interrogation region. Each tag reading device's 18 signal is limited to a particular area within the retail pharmacy, thereby allowing the detected signal to indicate the location of the prescription order within the pharmacy.

Alternatively, the tag 16 can include an internal power source and signal generator capable of transmitting a signal, which is read by the tag reading device 18.

Each tag reading device 18 is placed in communication with the computer system such that information regarding the customer, his prescription order position, and the status of his order can be readily displayed on the computer system display 22, and thereby facilitate location of the prescription order 10 within the pharmacy 14.

Preferably, the tags are attached to the prescription label 42 (FIG. 6A), detachably secured to the prescription order 44, or rigidly secured to a carrier 46 (FIG. 6C) containing these documents and other materials related to filling the prescription. The tags themselves can be either rigidly or detachably secured to the prescription order. For example, the tags can be directly secured to the prescription with adhesive or secured within a prescription lid. Also, the tags can be secured to a fastener, such as a paperclip, that is detachably secured to the prescription order.

B. Exemplar Pharmacy Prescription Order Filling Procedure

Figure 2:
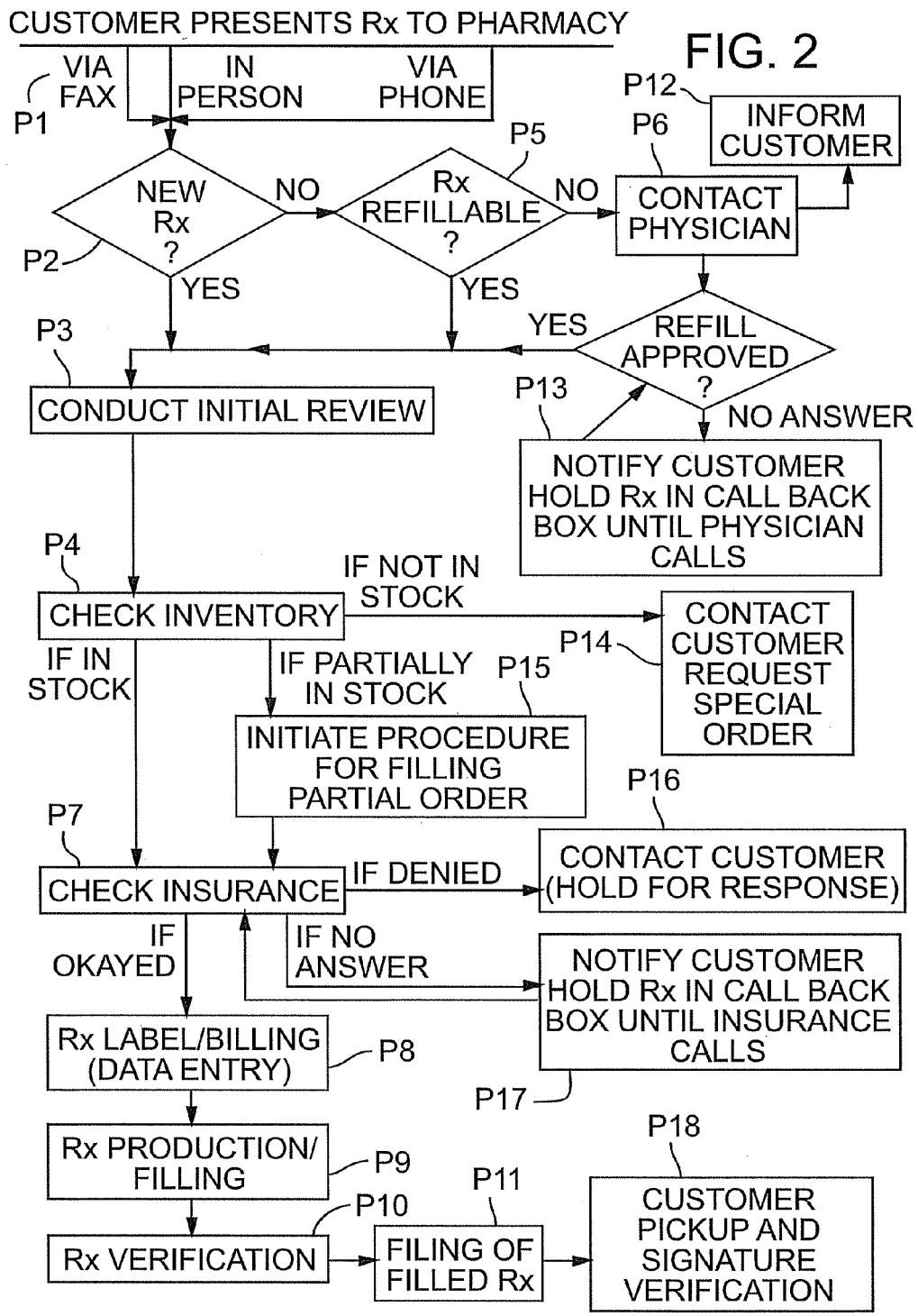
FIG. 2 is a block diagram of a pharmacy prescription order filling system in accordance with a preferred embodiment of the present invention.
Figure 6A:
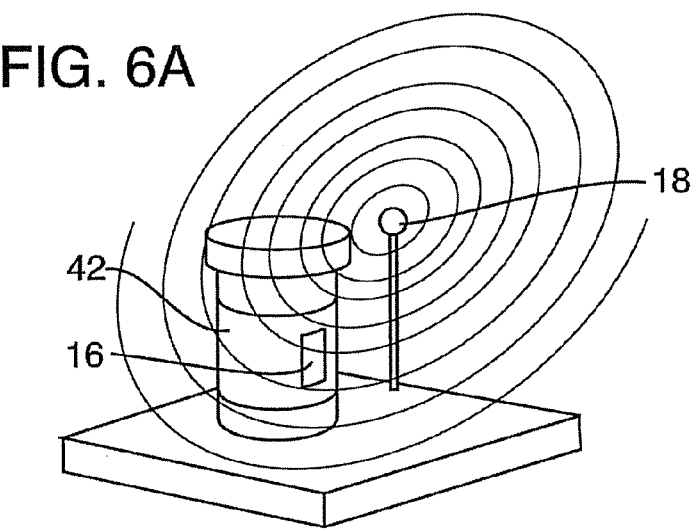
FIG. 6A is an isometric view of a first preferred embodiment showing a tracking tag being attached to a prescription label which is attached to the filled prescription.
Figure 6B:
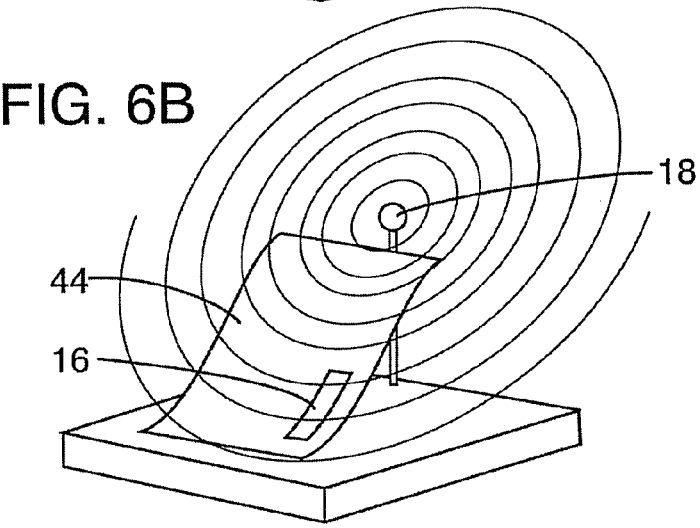
FIG. 6B is an isometric view of a second preferred embodiment showing a tracking tab being attached to a fastener, which is detachably secured to the prescription order.
Figure 6C:
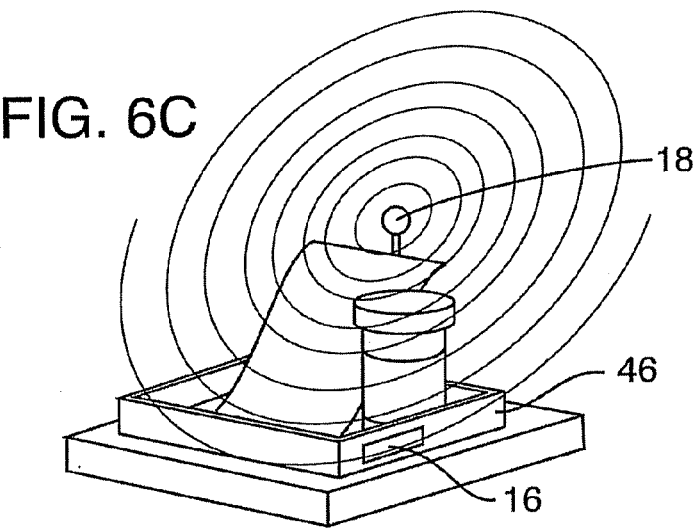
FIG. 6C is an isometric view of a third preferred embodiment showing a tracking tab being attached to a carrier containing a prescription order and materials related to filling the prescription order.

Referring specifically to FIG. 2, an exemplary pharmacy, which is preferably a retail pharmacy, prescription order filling procedure 24 is disclosed. In step P1, a prescription order, which could include a written prescription form 42 (FIG. 6A), a renewable prescription label 44 (FIG. 6B), or any other tangible medium documenting a request for a prescription by a health care provider is presented to the pharmacy either in person, via facsimile, via phone, or via a computer transmission, such as e-mail. A pharmacy worker then reviews the prescription order and attaches a unique tag 16 (FIG. 6A) to it that is readable by a tag reading device 18 (FIG. 6A) to determine its location within the pharmacy.

As shown in Step P2, the pharmacy worker then determines if the prescription order is for a new prescription. If so, the pharmacy worker conducts an initial review (Step P3) which includes checking the available inventory for the prescribed drug (Step P4), determining if there is available insurance (Step P7) and if required, obtaining approval from the insurer and preparing the label and necessary billing and information disclosure paperwork (Step P8).

If the prescription is not new, the pharmacy worker determines if it is refillable (Step P5). If so, the pharmacy worker then conducts the initial review (Step P3) as previously described. If not, the pharmacy worker contacts the prescribing health care provider (Step P6) to determine if the prescription may be refilled. If the health care provider approves of the refill, the pharmacy worker will then conduct the initial review (Step P3) as previously described. If not, the customer will be informed (Step P12). If the health care provider is not available, the prescription order to placed in a holding area until the health care provider is contacted (Step P13), and the customer is informed of this status.

Regarding Step P4, if the inventory is not in stock, the pharmacy worker typically informs the customer and offers the customer an opportunity to special order the prescribed drug (Step P14). If there is only a partial amount of the prescribed drug in stock, the pharmacy worker will typically initiate a procedure for filling only a partial order (Step P15). This procedure typically includes preparing additional paperwork to alert the customer that only a partial order has been filled, and ordering additional quantities of the prescribed drug.

Regarding Step P7, if the insurance coverage is denied, the prescription order is typically held in an area pending the customer being contacted to request authorization to proceed (Step P16). If the insurer cannot be contacted, the pharmacy has the option to either fill the prescription and alert the customer upon pick-up, or hold the prescription order pending a response from the insurer (Step P17).

After the initial review is complete, the prescription order and related paperwork are presented to a technician for filling (Step P9). The technician fills the prescription order and attaches the label. The technician then presents the filled prescription order and related paperwork to a registered pharmacist for verification (Step P10).

Following verification, the filled prescription is placed in a storage area pending customer pick-up (Step P11). When a customer picks-up the filled prescription, the pharmacy worker complies with applicable customer notice requirements, and obtains the customer's signature (also called "signature capture") confirming that they have received such notice (if applicable) and that they have received the filled prescription (Step P18).

C. Exemplar Pharmacy Tracking Zones

In practice and referring specifically to FIG. 1, it is more efficient to perform the various steps noted above at spaced apart locations, or zones, throughout the pharmacy. For example, prescription order intake (Step P1 of FIG. 2) and initial review (Step P3 of FIG. 2) can be performed at location Z1 (FIG. 1). Label printing and data entry (Step P8 of FIG. 2) could be accomplished at location Z2 (FIG. 1). Prescription orders waiting from some form of call back either from the customer, the insurer, or the health care provider could be placed at location Z3 (FIG. 1). Orders waiting to be filled could be placed at location Z4 (FIG. 1), orders waiting pharmacist review and approval could be place at location Z5 (FIG. 1), and approved filled prescription orders could be stored at location Z6 (FIG. 1). Obviously, additional zones (Z7 & Z8) could be added to accommodate a particular pharmacy's practices and procedures.

Preferably each station includes a tag reading device 18 in communication with the computer system 20 for automatically detecting the arrival of the tag 16 attached to the prescription order 12 as it enters each location. More preferably, the tag reading device 18 detects both the arrival of the tag 16 in that station, and the departure of that tag 16 from that station, with the time interval at that station being determined and recorded therefrom.

Each tag reading device 18 is preferably fixed at a particular location so that detecting the presence of a tag near the device also automatically indicates the location of that tag 16 within the pharmacy. The tag reading devices 18 can be rigidly mounted to a work area or station, or portable (i.e. handheld) devices that are operably connected to the station so that it can indicate a location within the pharmacy of a detected tag. Such portable devices facilitate scanning of prescription orders that are compiled in bulk, such as container of filled prescriptions where each prescription order in the container has a unique tag 18. Such a bulk container full of prescription order could arrive into the pharmacy from an off-site prescription filling station. In situations where the tag reading device can simultaneously detect and record the location of multiple prescription order, a pharmacy worker can wave the tag reading device 18 over the container to record the location of all prescription orders in the container.

D. Exemplar Storage Bin

Space and efficiency can be optimized by storing filled prescription orders 12 to be held for pick-up into a common storage bin 30. As best shown in FIG. 3, the storage bin 30 includes a plurality of cubbies 32, with each cubby 32 being sized to receive a prescription order 12 and associated filled prescription. Each cubby is uniquely identified 34, such as by being individually numbered, and includes a tag reading device 18 of determining whether a particular tag 16 is received within it. Each tag reading device 18 is in communication with the computer system 20.

When a prescription order 12 is filled, the prescription order 12 and filled prescription are simply inserted into an available cubby 32. Accordingly, the tag reading device 18 associated with that cubby 32 sends a signal to the computer system 20 denoting the particular location and cubby number where the prescription order 12 and filled prescription are held. When a customer arrives to pick-up his or her filled prescription, the worker enters the customer's identifying information into the computer system 20, and the particular bin number of the cubby containing the prescription order 12 and filled prescription or the current location in the filling process is displayed. The worker then locates and removes the filled prescription from the identified cubby and presents it to the customer.

The removal of the prescription order 12 from that particular cubby 32 is detected by the tag reading device 18 and reported to the computer system 20. The tag 16 can remain affixed to the prescription order 12 when filed, thereby allowing it to be easily located in the future. Alternatively, the tag 16 may be reused with a new incoming prescription order.

E. Exemplar Computer System

Those skilled in the art will appreciate that an exemplary embodiment of the present invention relies on and incorporates several common features of modern personal computers. The general use, operation, and construction of a computer system is known and has been disclosed in numerous patents such as U.S. Pat. No. 5,818,447 to Wolf et al. and U.S. Pat. No. 5,752,025 to Shakib et al., the disclosures of which are hereby incorporated by reference.

Figure 7:
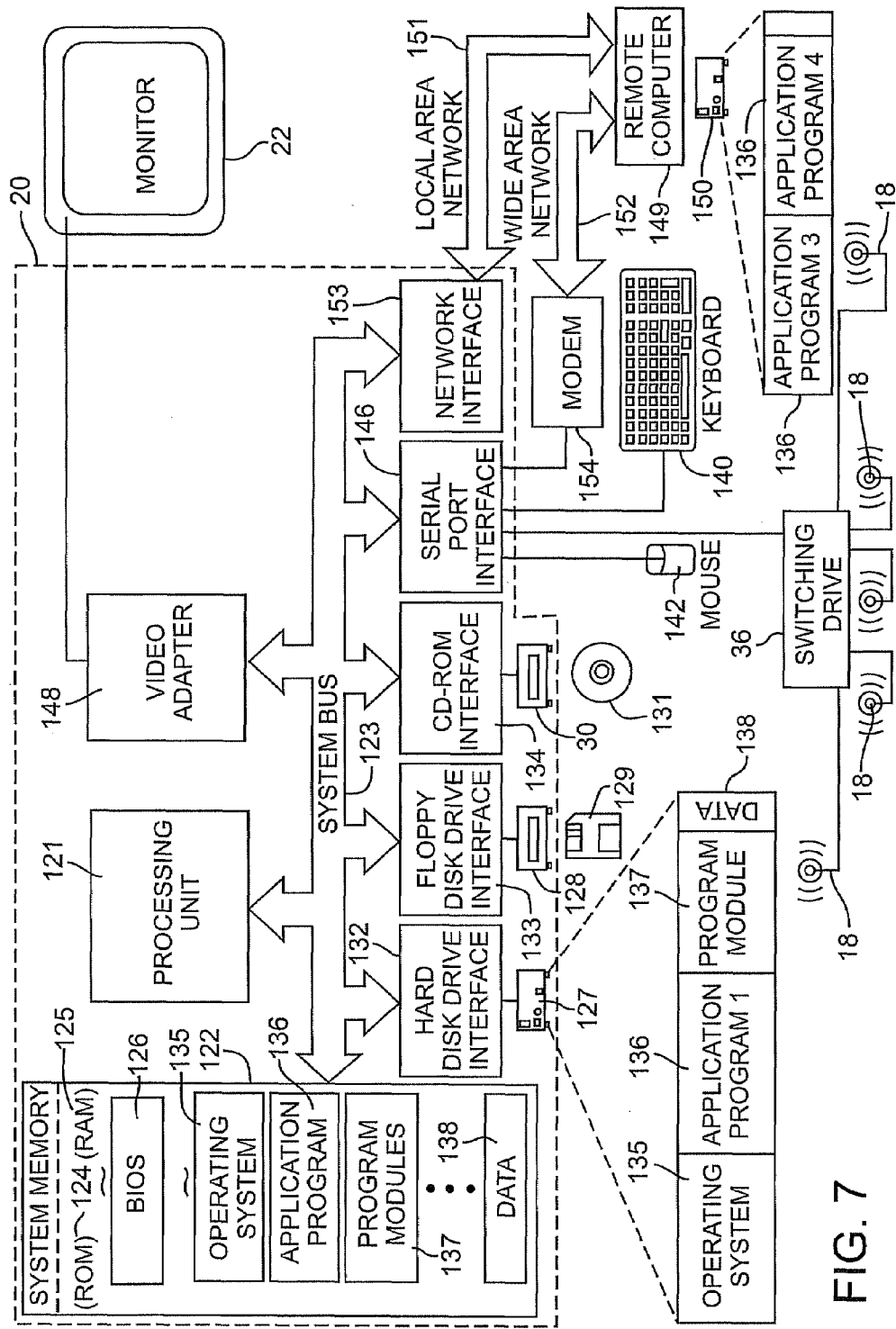
FIG. 7 is a block diagram of an exemplary computer system in accordance with a preferred embodiment of the present invention.

Referring to FIG. 7, the following discussion is intended to provide a brief, general description of a suitable computing environment in which the invention may be implemented. Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

With reference to FIG. 7, an exemplary system for implementing the invention includes a general purpose computing system in the form of a conventional personal computer 20, including a processing unit 121, a system memory 122, and a system bus 123 that couples various system components including the system memory to the processing unit 121. The system bus 123 may be any of several types of bus structures including a memory bus or memory controller, a peripheral bus, and a local bus using any of a variety of bus architectures. The system memory includes read only memory (ROM) 124 and random access memory (RAM) 125. A basic input/output system 126 (BIOS), containing the basic routines that help to transfer information between elements within the personal computer 20, such as during start-up, is stored in ROM 124. The personal computer 20 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of computer readable instructions, data structures, program modules and other data for the personal computer 120. Although the exemplary environment described herein employs a hard disk, a removable magnetic disk 129 and a removable optical disk 131, it should be appreciated by those skilled in the art that other types of computer readable media which can store data that is accessible by a computer, such as magnetic cassettes, flash memory cards, digital video disk, Bernoulli cartridges, random access memories (RAMs), read only memories (ROM), and the like, may also be used in the exemplary operating environment.

A number of program modules may be stored on the hard disk, magnetic disk 129, optical disk 131, ROM 124 or RAM 125, including an operating system 135, one or more application programs 136, other program modules 137, and program data 138. A user may enter commands and information into the personal computer 20 through input devices such as a keyboard 140, pointing device 142, and tag reading devices 18. Preferably, a plurality of tag reading devices 18, which are distributed throughout the pharmacy are integrated with a switching device 36 that periodically monitors the status of each tag reading device 18 and transmits that information to the personal computer 20. Other input devices (not shown) may include a microphone, joystick, game pad, satellite dish, scanner, or the like.

These and other input devices are often connected to the processing unit 121 through serial port interface 146 that is coupled to the system bus, but may be connected by other interfaces, such as a parallel port, game port or a universal serial bus (USB). A monitor 147 or other type of display device is also connected to the system bus 123 via an interface, such as a video adapter 148. In addition to the monitor, personal computers typically include other peripheral output devices (not shown), such as speakers and printers.

The personal computer 20 may operate in a networked environment using logical connections to one or more remote computers, such as a remote computer 149. The remote computer 149 may be another personal computer, a server, a router, a network PC, a peer device, a personal digital assistant ("PDA"), or other common network node, and typically includes many or all of the elements described above relative to the personal computer 20, although only a memory storage device 150 has been illustrated in FIG. 7. The logical connections depicted in FIG. 7 include a local area network (LAN) 151 and a wide area network (WAN) 152. Such networking environments are commonplace in offices, enterprise-wide computer networks, intranets and the Internet.

When used in a LAN networking environment, the personal computer 20 is connected to the local network 151 through a network interface or adapter 153. When used in a WAN networking environment, the personal computer 20 typically includes a modem 154 or other means for establishing communications over the wide area network 152, such as the Internet. The modem 154, which may be internal or external, is connected to the system bus 123 via the serial port interface 146. In a networked environment, program modules depicted relative to the personal computer 20, or portions thereof, may be stored in the remote memory storage device. It will be appreciated that the network connections shown are exemplary and other means of establishing a communications link between the computers may be used.

Preferably, a plurality of networked personal computers 20 are positioned within the pharmacy, one at the intake area (Z1, FIG. 1), one at the customer pick-up area (Z9, FIG. 1), and one at the data entry/label area (Z2, FIG. 1).

F. Preferred Application Program

The detailed description which follows is represented largely in terms of processes and symbolic representations of operations by conventional computer components, including a processing unit, memory storage devices for the processing unit, and a display device. These operations include the manipulation of data bits by the processing unit and the maintenance of these bits within data structures resident in one or more of the memory storage devices. Such data structures impose a physical organization upon the collection of data bits stored within memory and represent specific electrical or magnetic elements. These symbolic representations are the means used by those skilled in the art of computer programming and the construction of computing devices to most effectively convey teachings and discoveries to others skilled in the art.

For purposes of this discussion, a process is generally a sequence of steps executed by a computing device leading to a desired result. These steps generally require physical manipulations of physical quantities. Usually, although not necessarily, these quantities take the form of electrical, magnetic, or optical signals capable of being stored, transferred, combined, compared, or otherwise manipulated. It is conventional for those skilled in the art to refer to these signals as bits, values, elements, symbols, characters, terms, numbers, records, files or the like. It should be kept in mind however, that these and similar terms should be associated with appropriate physical quantities for computing device operations, and that these terms are merely conventional labels applied to physical quantities that exist within and during operation of the computing device.

It should also be understood that manipulations within the computing device are often referred to in terms such as adding, comparing, moving, etc. which are often associated with manual operations performed by a human operator. The operations described herein are machine operations performed in conjunction with a human operator or user that interacts with a control device. The machines used for performing the operation of the preferred embodiment of the present invention, as will be understood, include a control device and other suitable input devices.

Figure 8:
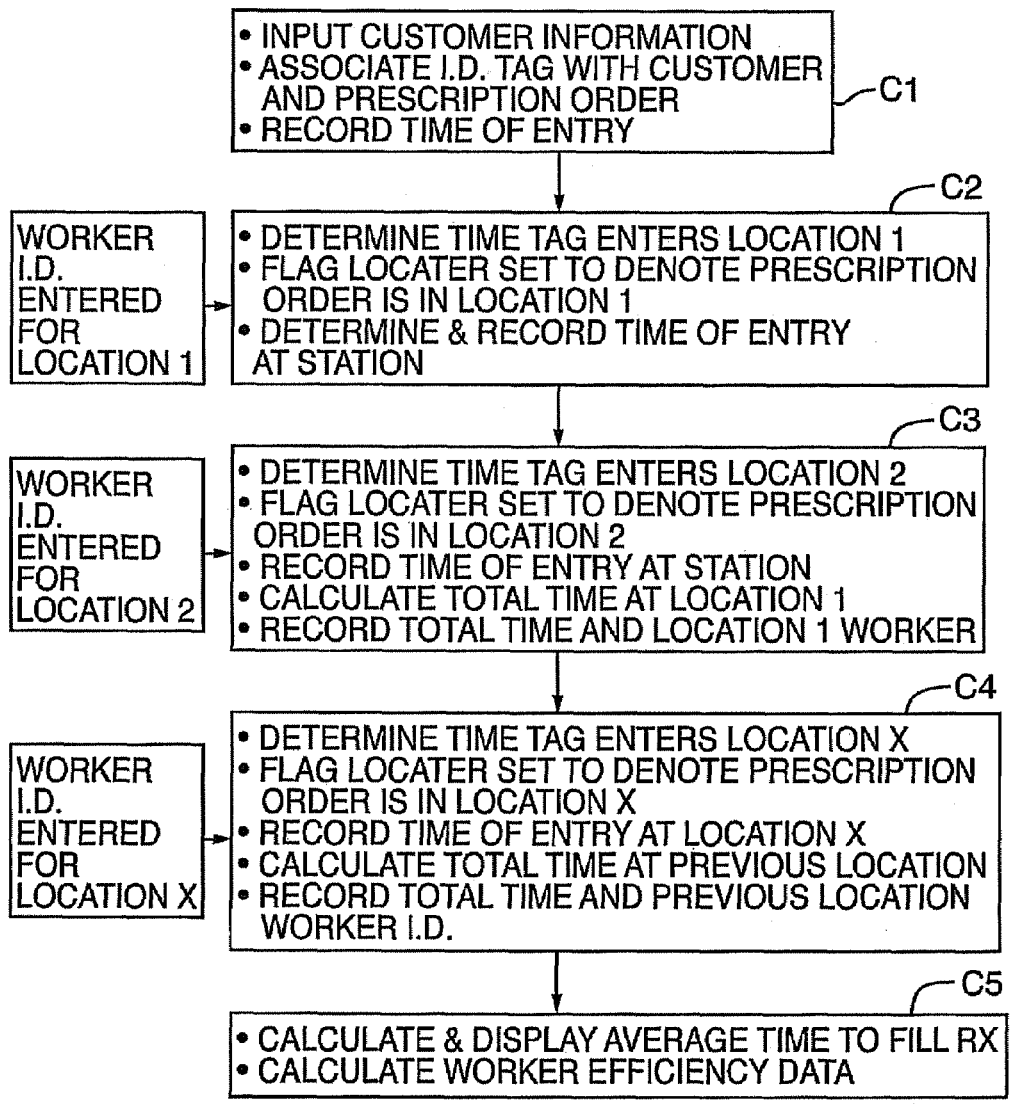
FIG. 8 is a block diagram of an exemplary application program in accordance with a preferred embodiment of the present invention.

The preferred method of performing the invention is best described in the flowchart of FIG. 8. In general, in step C1, the computer system 20 initially associates a particular customer with a tag, which has been attached to the prescription order. Preferably, the time of entry, and name or employee number of the worker accepting the prescription order is also recorded and stored in memory.

As the tag enters a first location within the pharmacy, a signal is transmitted from the tag reading device at that location to the computer system (Step C2, FIG. 8). In response to the input signal from the tag reading device, the system updates a location flag to denote that the tag, and its associated prescription order, are currently in that location. The time of entry into that location is also noted, and the name of the worker assigned to that location is noted and stored in memory. More preferably, the tag reading device at that location also detects when the tag has left the station, and updates the location flag to denote that the tag is no longer at that station. In such case, the time the tag left the station is also noted.

As the tag moves from the first location to a second location, a signal is transmitted from the tag reading device at the second location to the computer system (Step C3, FIG. 8). In response to the input signal from the tag reading device, the computer system 20 updates the location flag to denote the new location of the tag, and its associated prescription order. The time of entry into that location is noted, and the name of the worker assigned to that location is noted and stored in memory. More preferably, the tag reading device at the second location also detects when the tag has left that station, and updates the location flag to denote that the tag is no longer at that station.

This process continues as the tag and attached prescription order move through the various locations within the retail pharmacy (Step C4).

This stored data can then be used to determine the location of the prescription order within the pharmacy. Moreover, the corresponding time and worker information can also be readily compiled to track pharmacy performance (Step C5). For example, the average time it takes for prescriptions to be filled over a given time frame can be readily determined and displayed to workers or customers, thereby giving them an accurate estimate of how long it will really take for the pharmacy to fill a prescription order. Moreover, the efficiency of each worker at each location can be determined, thereby allowing pharmacy management to more effectively monitor work flow and productivity issues.

Similarly, this information can be readily used to automatically monitor the amount of time filled prescription orders remain in their cubbies. Most prescription insurers require that, if possible, filled prescription orders be returned to stock if they are not picked-up within a set number of days, and the cost of that prescription be credited back to them. The present system can automatically monitor the time a filled prescription has remained in the storage area, flag any filled prescriptions that are overdue for pick-up, and notify the pharmacy worker of the need to return that particular filled prescription to stock.

In addition, in situations where the tag remains secured to the filled prescription following customer pick-up, the system can automatically detect when that prescription is returned by that customer to be refilled simply by the customer presenting the empty prescription vial to the pharmacy. Accordingly, the system can automatically monitor whether the requested refill is premature under either insurance rules or pursuant to the health care provider's instructions. If so, the system will automatically notify the pharmacy worker of this discrepancy.

In view of the wide variety of embodiments to which the principles of the invention can be applied, it should be apparent that the detailed embodiments are illustrative only and should not be taken as limiting the scope of the invention. Rather, the claimed invention includes all such modifications as may come within the scope of the following claims and equivalents thereto.

What is claimed is:

1. A method for tracking physical location of prescription orders through a pharmacy having a plurality of physically spaced apart locations for manually filling and storing the prescription orders, the plurality of spaced apart locations being positioned along a workflow stream leading to a storage area with an array of compartments for storing filled prescription orders therein, prescription orders being moved between the plurality of spaced apart locations by one or more pharmacy workers by hand, said method including the following steps:

receiving plural prescription orders at a first location upstream of the storage area;

operably securing a separate machine-readable tag to each prescription order upstream of said storage area, each said tag having a unique identifier that is readable by a tag reader in proximity to the tag regardless of its orientation relative to the tag reader;

associating the unique identifier of each tag with customer information stored in a computer system in association with the prescription order;

moving the prescription orders by hand to a second location within the pharmacy for manual filling upstream of the storage area, the second location having a second location tag reader in communication with the computer system;

automatically detecting the presence of the prescription orders at the second location by reading the unique identifier of the remote tags with said second location tag reader regardless of the orientation of said tags and automatically recording at the computer system the location of the prescription orders at said second location for the manual filling;

moving each of the prescription orders by hand to one of the compartments in the array of compartments as a filled prescription order, each compartment having a corresponding compartment tag reader that is in communication with the computer system and is operable to read the unique identifier of the tag on the filled prescription order regardless of the orientation of the tag, whereby the step of associating the unique identifier of each tag with customer information and the step of automatically detecting the presence of the prescription orders are performed by or under control of the computer system.

2. A method for tracking physical location of prescription orders through a pharmacy of claim 1, further including the steps of:

displaying on a computer system the compartment in which any selected prescription order is stored, thereby facilitating the easy location of said prescription order.

3. A method for tracking physical location of prescription orders through a pharmacy of claim 1, further including the steps of:

automatically collecting timing information about the amount of time each of the prescription orders remains at the second location;

storing said timing information into the computer system; and, compiling workflow information based on the timing information.

4. A method for tracking physical location of prescription orders through a pharmacy of claim 3, further including the step of:

associating the workflow information with a particular worker to evaluate worker efficiency.

5. A method for tracking physical location of prescription orders through a pharmacy of claim 1, wherein said pharmacy is a retail pharmacy.

6. A method for ensuring that a pharmacy worker distributes the correct prescription order to a customer of the pharmacy, the pharmacy having a storage portion with an array of individually identified storage areas therein, each individually identified storage area having a unique visual identifier, said method comprising:

receiving a prescription order at a first location spaced apart from the storage area within the pharmacy;

operably securing a machine-readable tag to the prescription order, the machine-readable tag having a unique tag identifier readable when placed in proximity to a tag reader regardless of orientation of the tag relative to the tag reader;

associating the machine-readable tag with customer information associated with the prescription order in the computer system;

manually filling the prescription order defining a filled prescription order;

placing the filled prescription order and the machine-readable tag by hand into one individually identified storage area of the plurality of individually identified storage areas without instructions from the computer system as to which individually identified storage area the filled prescription order and the machine-readable tag are to be placed into thereby defining a pharmacy worker selected storage area;

reading the unique tag identifier of the tag within the pharmacy worker selected storage area with a tag reader that is associated with the pharmacy worker selected storage area, but not with any other individually identified storage areas in the array;

providing the unique tag identifier and the storage area identifier for the pharmacy worker selected storage area to the computer system;

the computer system correlating the customer information, unique tag identifier, and storage area identifier;

retrieving the customer information from the computer system to determine the storage area identifier associated with the pharmacy worker selected storage area in which the customer's filled prescription order is located; and, retrieving the filled prescription order by hand from the identified pharmacy worker selected storage area of the storage portion.

7. The method of claim 6, wherein said tag is a radio-frequency identification ("RFID") tag and said tag readers are RFID readers.

8. The method of claim 6, wherein said storage area identifier is not related to information contained within the customer information.

9. The method of claim 6, wherein said storage area identifier is numeric.

10. The method of claim 6, further including:

detecting the removal of the filled prescription order and its associated tag from the pharmacy worker selected storage area by the tag reader associated with the pharmacy worker selected storage area.

11. The method of claim 10, further including:
monitoring with the computer system the time the filled prescription order and its associated tag remains within the pharmacy worker selected storage area; and
returning the filled prescription order to stock if the prescription order is not picked up within a predefine time limit.

12. The method of claim 6, further including placing a second filled prescription order with a second unique remote tag operably secured thereto within the pharmacy worker selected storage area such that the filled prescription order and the second filled prescription order concurrently occupy the same pharmacy worker selected storage area, and wherein the computer system associates customer identifying information for the second filled prescription, the second prescription order and the storage identifier.

13. The method of claim 12, wherein the computer system detects the removal of the prescription order from the pharmacy selected storage area during the retrieving the prescription order step, and detects the continued presence of the second prescription order within the pharmacy selected storage area during the retrieving the prescription order step.

14. A method for tracking physical location of prescription orders through a pharmacy having a plurality of physically spaced apart locations for manual filling and storing the prescription orders, the plurality of spaced apart locations being positioned along a workflow stream leading to a storage area with an array of compartments for storing filled prescription orders therein, prescription orders being moved between the plurality of spaced apart locations by one or more pharmacy workers by hand, said method including the following steps:
receiving plural prescription orders at a first location upstream of the storage area;
operably securing machine-readable tags to the prescription orders upstream of said storage area, each said tag having a unique identifier that is readable by a tag reader in proximity to the tag regardless of its orientation relative to the tag reader;
associating the unique identifiers of the tags with customer information stored in a computer system in association with the prescription orders;
moving the prescription orders by hand to a second location within the pharmacy for manual filling upstream of the storage area, the second location having a second location tag reader in communication with the computer system;
automatically detecting the presence of the prescription orders at the second location by reading the unique identifier of the remote tags with said second location tag reader regardless of the orientation of said tags and automatically recording at the computer system the location of the prescription orders at said second location for manual filling; and
moving the prescription orders by hand to one or more of the compartments in the array of compartments as filled prescription orders, each compartment having a corresponding compartment tag reader that is in communication with the computer system and is operable to read the unique identifier of the tag on each filled prescription order in the compartment regardless of the orientation of the tag,
whereby the step of associating the unique identifier of each tag with customer information and the step of automatically detecting the presence of the prescription orders are performed by or under control of the computer system.

15. A method for tracking physical location of prescription orders through a pharmacy of claim 14, further including the steps of:
displaying on a computer system the compartment in which any selected prescription order was stored by hand, thereby facilitating the easy location of said prescription order by a pharmacy worker.

16. The method of claim 14, further including:
detecting removal of a filled prescription order and its associated tag from a selected compartment in the storage area with the compartment tag reader corresponding to the selected compartment.

* * * * *

UNITED STATES PATENT AND TRADEMARK OFFICE
CERTIFICATE OF CORRECTION

| | | |
|---|---|---|
| PATENT NO. | : 7,672,859 B1 | Page 1 of 1 |
| APPLICATION NO. | : 09/715439 | |
| DATED | : March 2, 2010 | |
| INVENTOR(S) | : Shelton Louie et al. | |

It is certified that error appears in the above-identified patent and that said Letters Patent is hereby corrected as shown below:

In the Specification:

Column 5, line 59, "to" should read --is--.

Column 6, line 36, "from" should read --for--.

Column 6, line 40, "place" should read --placed--.

Column 6, line 64, "order" should read --orders--.

Column 6, line 67, "order" should read --orders--.

In the Claims:

Column 13, line 6, "predefine" should read --predefined--.

Signed and Sealed this
Twenty-first Day of April, 2015

Michelle K. Lee
*Director of the United States Patent and Trademark Office*